US009597524B2

(12) United States Patent
Jorgenson et al.

(10) Patent No.: US 9,597,524 B2
(45) Date of Patent: Mar. 21, 2017

(54) DEFIBRILLATOR WITH DYNAMIC ONGOING CPR PROTOCOL

(75) Inventors: Dawn Jorgenson, Mercer Island, WA (US); Christian Cary, Sammamish, WA (US); Jamie Froman, Issaquah, WA (US); Kenneth Rucker, Mill Creek, WA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 786 days.

(21) Appl. No.: 13/881,380

(22) PCT Filed: Oct. 26, 2011

(86) PCT No.: PCT/IB2011/054772
§ 371 (c)(1),
(2), (4) Date: Apr. 25, 2013

(87) PCT Pub. No.: WO2012/059846
PCT Pub. Date: May 10, 2012

(65) Prior Publication Data
US 2013/0218057 A1 Aug. 22, 2013

Related U.S. Application Data

(60) Provisional application No. 61/409,808, filed on Nov. 3, 2010, provisional application No. 61/466,512, filed on Mar. 23, 2011.

(51) Int. Cl.
*A61N 1/00* (2006.01)
*A61N 1/39* (2006.01)
*A61H 31/00* (2006.01)

(52) U.S. Cl.
CPC ......... *A61N 1/3925* (2013.01); *A61H 31/005* (2013.01); *A61N 1/3987* (2013.01)

(58) Field of Classification Search
CPC ... A61H 31/005; A61N 1/3925; A61N 1/3987
See application file for complete search history.

(56) References Cited

U.S. PATENT DOCUMENTS 5,957,856 A * 9/1999 Weil .................. A61N 1/39
600/518
2006/0069326 A1 3/2006 Heath
(Continued)

FOREIGN PATENT DOCUMENTS

JP 2005339533 A 12/2005
WO 2005112749 A1 12/2005
(Continued)

*Primary Examiner* — Niketa Patel
*Assistant Examiner* — Lindsey G Hankins

(57) ABSTRACT

An automated external defibrillator (AED) (10) having a treatment decision processor (28) is described which follows a "shock first" or a "CPR first" rescue protocol after identification of a treatable arrhythmia, depending upon an estimate of the probability of successful resuscitation made from an analysis of a patient parameter measured at the beginning of the rescue. The invention may also follow different CPR protocols depending on the estimate. The invention also may use the trend of the measured patient parameter to adjust the CPR protocol either during a CPR pause or after the initial CPR pause. The AED (10) thus enables an improved rescue protocol.

12 Claims, 9 Drawing Sheets

(56) References Cited

U.S. PATENT DOCUMENTS

| | | |
|---|---|---|
| 2006/0229680 A1 | 10/2006 | Chapman et al. |
| 2008/0176199 A1 | 7/2008 | Stickney et al. |
| 2008/0215102 A1* | 9/2008 | Myklebust ............ A61H 31/005 607/6 |
| 2009/0024175 A1* | 1/2009 | Freeman ................ A61H 31/00 607/6 |
| 2010/0022886 A1 | 1/2010 | Ayati et al. |

FOREIGN PATENT DOCUMENTS

| | | |
|---|---|---|
| WO | 2006136974 A2 | 12/2006 |
| WO | 2007069162 A1 | 6/2007 |
| WO | 2008068694 A1 | 6/2008 |
| WO | 2008086496 A2 | 7/2008 |

* cited by examiner (1-263) PASclean = no shock; (264-363) PASclean = chock 1-239 PAScpr = no shock; 240-323 PAScpr = chock

DEFIBRILLATOR WITH DYNAMIC ONGOING CPR PROTOCOL

This application is a U.S. National Phase Application of International Application No. PCT/IB2011/054772, filed on Oct. 26, 2011, and claims the benefit of U.S. Provisional No. 61/409,808, filed on Nov. 3, 2010, and U.S. Provisional No. 61/466,512, filed on Mar. 23, 2011.

The invention relates generally to electrotherapy circuits, and more particularly, to a defibrillator which analyzes patient physiological data and determines whether a shock or cardio-pulmonary resuscitation (CPR) therapy should be conducted. More specifically, an AED rhythm classification, such as a so-called vRhythm score determines the optimal protocol for CPR, deciding whether, for example, compressions-only CPR or conventional CPR (compressions+breaths) should be performed by the responder. The trend of the vRhythm score may be utilized to adjust the CPR protocol during the rescue. In addition, the AED rhythm classification may be used during CPR to help determine whether to stop the CPR period early in order to deliver an immediate defibrillating shock.

Defibrillators deliver a high-voltage impulse to the heart in order to restore normal rhythm and contractile function in patients who are experiencing arrhythmia, such as ventricular fibrillation ("VF") or ventricular tachycardia ("VT") that is not accompanied by spontaneous circulation. There are several classes of defibrillators, including manual defibrillators, implantable defibrillators, and automatic external defibrillators ("AEDs"). AEDs differ from manual defibrillators in that AEDs can automatically analyze the electrocardiogram ("ECG") rhythm to determine if defibrillation is necessary. In nearly all AED designs, the user is prompted to press a shock button to deliver the defibrillation shock to the patient when a shock is advised by the AED.

FIG. 1 is an illustration of a defibrillator 10 being applied by a user 12 to resuscitate a patient 14 suffering from cardiac arrest. In sudden cardiac arrest, the patient is stricken with a life threatening interruption to the normal heart rhythm, typically in the form of VF or VT that is not accompanied by spontaneous circulation (i.e., shockable VT). In VF, the normal rhythmic ventricular contractions are replaced by rapid, irregular twitching that results in ineffective and severely reduced pumping by the heart. If normal rhythm is not restored within a time frame commonly understood to be approximately 8 to 10 minutes, the patient will die. Conversely, the quicker that circulation can be restored (via CPR and defibrillation) after the onset of VF, the better the chances that the patient 14 will survive the event. The defibrillator 10 may be in the form of an AED capable of being used by a first responder. The defibrillator 10 may also be in the form of a manual defibrillator for use by paramedics or other highly trained medical personnel.

A pair of electrodes 16 are applied across the chest of the patient 14 by the user 12 in order to acquire an ECG signal from the patient's heart. The defibrillator 10 then analyzes the ECG signal for signs of arrhythmia. If VF is detected, the defibrillator 10 signals the user 12 that a shock is advised. After detecting VF or other shockable rhythm, the user 12 then presses a shock button on the defibrillator 10 to deliver defibrillation pulse to resuscitate the patient 14.

Recent studies have shown that different patients may be resuscitated more effectively with different treatment regimens depending upon various factors. One factor which affects the likelihood of success of defibrillation is the amount of time that has elapsed since the patient experienced the arrhythmia. This research has indicated that, depending on the duration of cardiac arrest, a patient will have a better probability of recovery with one protocol as compared to another. If the AED is set up for a less effective protocol for the resuscitation of a particular patient, that patient's probability of recovery may be reduced. These studies have shown that some of these patients have a better chance of being resuscitated if CPR is performed first, which will start by providing externally driven circulation which may bring the patient to a condition where application of a shock will be successful at restoring spontaneous circulation.

Various attempts have been made to try to make this determination in an automated way from the patient's vital signs. Since the determination of whether a shock is advised begins with analysis of the ECG waveform of the patient, these attempts have focused on analyzing the ECG waveform in order to make this determination. One line of studies has looked at the amplitude of the ECG waveform and found that patients with a stronger (higher amplitude) ECG waveform have a better chance of resuscitation with a defibrillating shock than do patients with a lower amplitude ECG. Since the amplitude of the ECG will generally decline with the passage of time after the onset of VF, this result is understandable. However, this measure is not a fail-proof predictor of resuscitation success. Another characteristic of the ECG which has been studied as a predictor of success is the frequency composition of the ECG waveform, with higher frequency content being found to correlate with resuscitation success. This analysis is done by performing a spectral analysis of the ECG waveform, as by using a fast Fourier transform processor to perform a spectral analysis of the ECG. This, too, has not been found to be a completely accurate predictor of success. Other researchers have multiplied amplitude and frequency information of the ECG with each other to produce a weighted high frequency measurement as a predictor of success, which takes advantage of both characteristics. Accordingly it is desirable to have a defibrillator determine a treatment regimen with a high probability of success automatically and with high accuracy.

It is further desirable to determine the treatment regimen quickly, as soon as the AED is attached to the patient. Failure to do so can lead to several problems. If, for example, a rescuer arrives at the scene with an AED set up to perform CPR first (i.e. prior to defibrillation) and finds that good CPR is already in progress, a defibrillation shock is unnecessarily delayed. On the other hand, if a rescuer arrives at the scene with an AED set up to deliver a shock-first (i.e. prior to CPR) and finds a long-downtime patient with no CPR in progress, CPR may be delayed. In each of these situations, the less optimal rescue protocol may reduce the likelihood of survival.

In addition, fixed intervals of cardiopulmonary resuscitation (CPR) without pause for ECG analysis reduce "hands-off" time but risk delaying defibrillation in cases of failed shocks and re-fibrillation, with unknown consequence for patient outcomes. Some patients with shockable rhythms during CPR may benefit from an early shock, but interrupting CPR for analysis could compromise more patients. Thus what is needed is an analysis algorithm for detecting shockable rhythms with high likelihood of return of spontaneous circulation (ROSC) that optimizes the duration of CPR. This invention uses two existing algorithms in combination: an AED shock advisory algorithm designed for high specificity, and an index of ECG rate of change that is indicative of the likelihood of ROSC after a defibrillation shock. Embodiments of the analysis algorithm are described in co-assigned and co-pending U.S. application Ser. No. 11/917,272, entitled "Defibrillator with Automatic Shock First/CPR First Algorithm", which is herein incorporated by reference.

In addition, it is known that responders often have trouble performing rescue breaths during CPR and that hands-only CPR can be very effective. It is also known that continuous compressions with minimal interruptions (e.g., giving breaths) can result in improved resuscitation. A problem inherent in existing rescue defibrillators is that the defibrillator is unable to determine which CPR protocol to pursue (compressions-and-breaths or compressions-only) for optimal survival.

Because CPR causes artifact in the ECG, reliable determination of onset of re-fibrillation during CPR is not possible with present technology. Current cardiopulmonary resuscitation guidelines recommend periods of uninterrupted CPR, hence a pause in CPR to analyze the ECG is undesirable, and might adversely affect patient survival. On the other hand, in patients who re-fibrillate during CPR, prolonged CPR may adversely affect survival. Because the fraction of patients who would benefit from a pause in CPR to confirm a shockable rhythm is small compared to the majority for whom continued CPR is beneficial, an algorithm that can determine a high likelihood of the presence of a shockable rhythm during CPR artifact (i.e. without a pause) would allow identifying patients who might benefit from a shock without compromising resuscitation for the majority of patients.

In accordance with the principles of the present invention, a defibrillator is described which automatically analyzes an ECG waveform and estimates a likelihood of return of spontaneous circulation (ROSC) score. The ROSC score is compared to a threshold to advise a treatment regimen which is more likely to be successful. The treatment regimen can be to shock the patient first, then analyze the ECG further and possibly provide CPR. Another possible treatment regimen is to provide CPR to the patient before delivering a shock.

The present invention further exploits the inventors' discovery that the ROSC score correlates well with the probability of the patient survival. In particular, the inventors have discovered that a ROSC score that improves during a rescue generally indicates a higher likelihood of patient survival. Thus, the trend of the ROSC score during rescue may be used to adjust the CPR protocol throughout the rescue in order to improve the patient's outcome.

The present invention further recognizes that if a patient is in VF it may be optimal to give hands-only CPR. If a patient is in a non-shockable rhythm, it may be optimal to give compressions plus breaths. The ROSC score may enhance this by adding value in that the "vitality" of the VF is indicated by the ROSC score. If the ROSC score indicates longer down-time (less vitality) it may be that only compressions should be provided or breaths and compressions. In the case of a non-shockable rhythm, it may be that breaths and compressions should be provided. For some rhythms (e.g., bradycardia less than 40 BPM) breaths may be indicated. In accordance with the principles of the invention, one object of the invention is to describe a defibrillator and a method for delivering electrotherapy which utilizes a ROSC score to select one of a plurality of CPR modes of operation. For example, the defibrillator may select a compressions-only mode of CPR operation for ROSC scores above a threshold, or may select a compressions-plus-breath mode of CPR operation for ROSC scores below the threshold. The threshold may be adjustable to comport with the particular protocol of the local rescue authority.

Another object of the invention is a defibrillator and method which compares successive ROSC estimates to determine whether a change from a first CPR mode of operation to a second CPR mode of operation would be beneficial to the patient. For example, if the ROSC estimate worsens during the course of a cardiac rescue, the defibrillator may change the CPR mode of operation from a compressions-only mode to a compressions-plus-breath mode of operation.

Yet another object of the invention is a defibrillator and method which calculates successive ROSC estimates prior to and just subsequent to a defibrillating shock, and supplements the shock mode of operation with a supplemental shock based on the comparison. For example, it may be beneficial to immediately deliver a second shock in what would otherwise be a single-shock protocol if the subsequent ROSC estimate is higher than the prior ROSC estimate.

Yet another object of the invention is a defibrillator and method which calculates successive ROSC estimates, and issues user feedback based on the comparison. For example, aural or visual feedback of "Good CPR" or "improving patient" may be issued by the defibrillator if the successive ROSC score is higher than the prior ROSC score.

Yet another object of the invention is a defibrillator and method which calculates a ROSC estimate during CPR compressions and determines whether CPR should be interrupted to deliver an immediate electrotherapy shock. In order to minimize the deleterious effect of an erroneous determination, e.g. due to CPR artifact, one embodiment of the invention confirms the determination after CPR is interrupted, and thereafter adjusts the determination criteria if the determination was erroneous. The adjustment can be to disable the interruption feature altogether.

Yet another object of the invention is a defibrillator which implements the ROSC scoring processor in an efficient manner and which produces a ROSC score quickly and conveniently.

IN THE DRAWINGS

Figure 11:
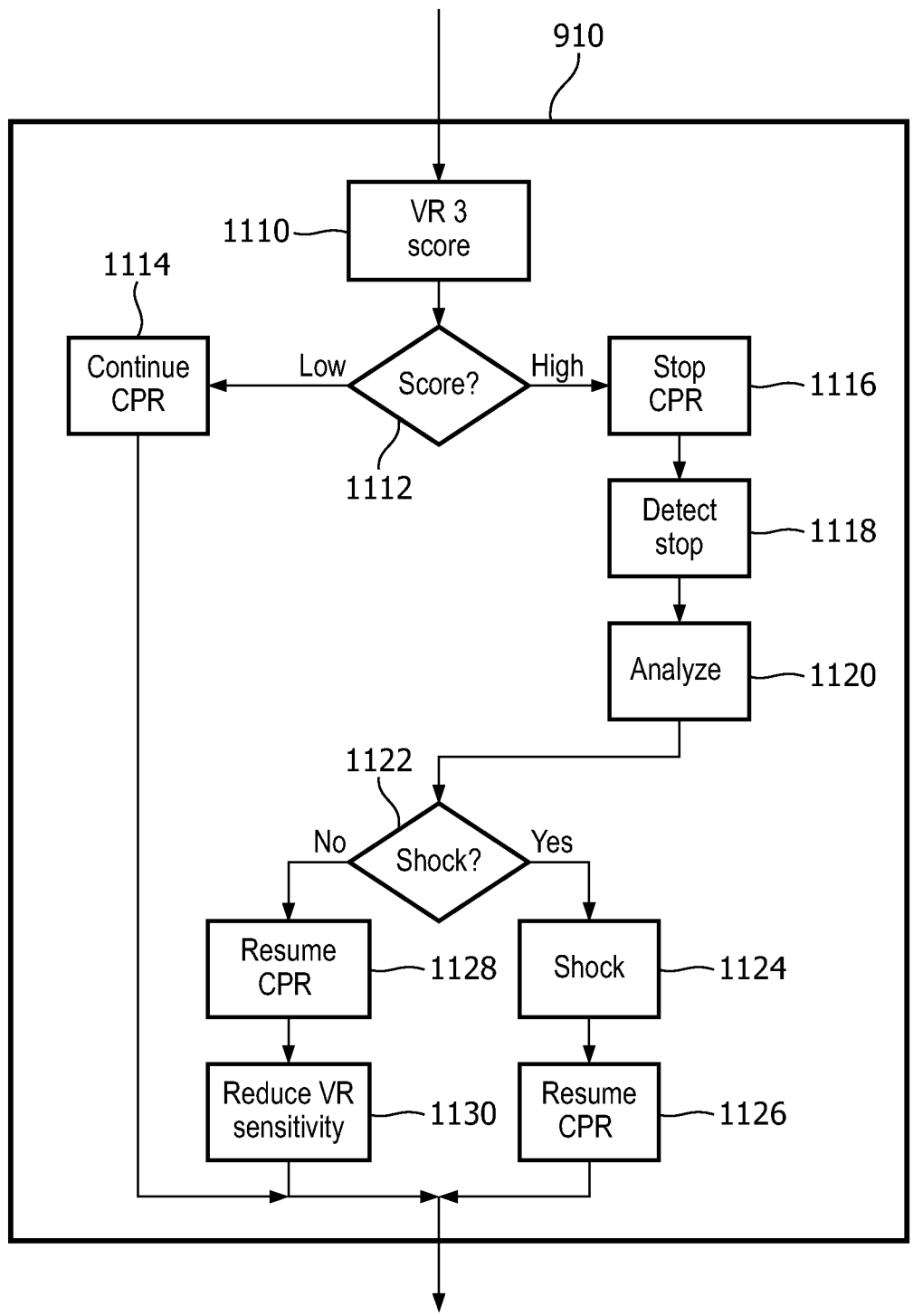

FIG. 11 illustrates a flow diagram illustrating the use of vRhythm during a CPR period. In the FIG. 11 embodiment, a ROSC score is calculated during CPR and causes an interruption of CPR if the score indicates that an immediate shock is beneficial. Otherwise, CPR continues to the conclusion of the CPR period.

Figure 1:
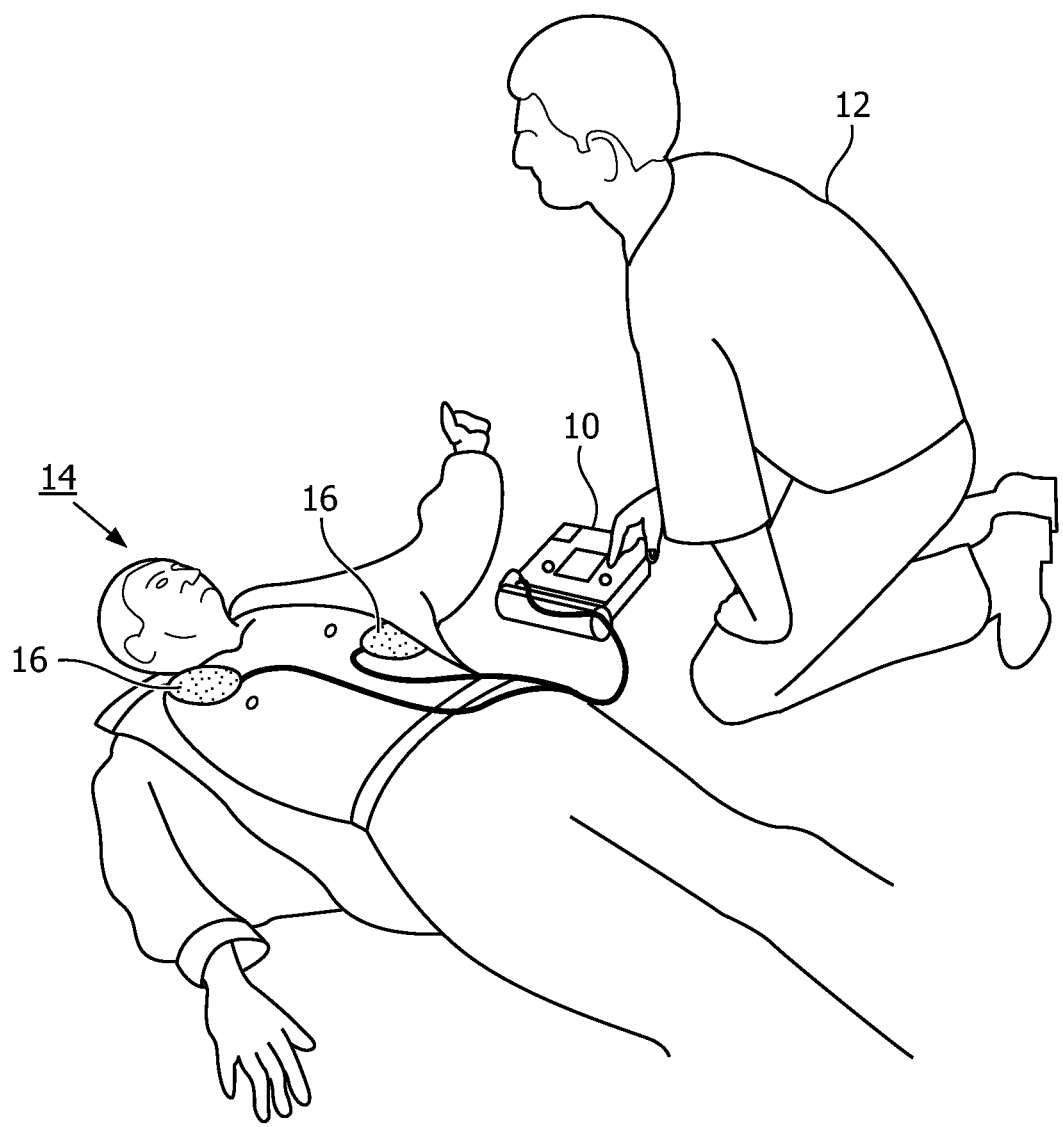
FIG. 1 is an illustration of a defibrillator being applied to a patient suffering from cardiac arrest.
Figure 2:
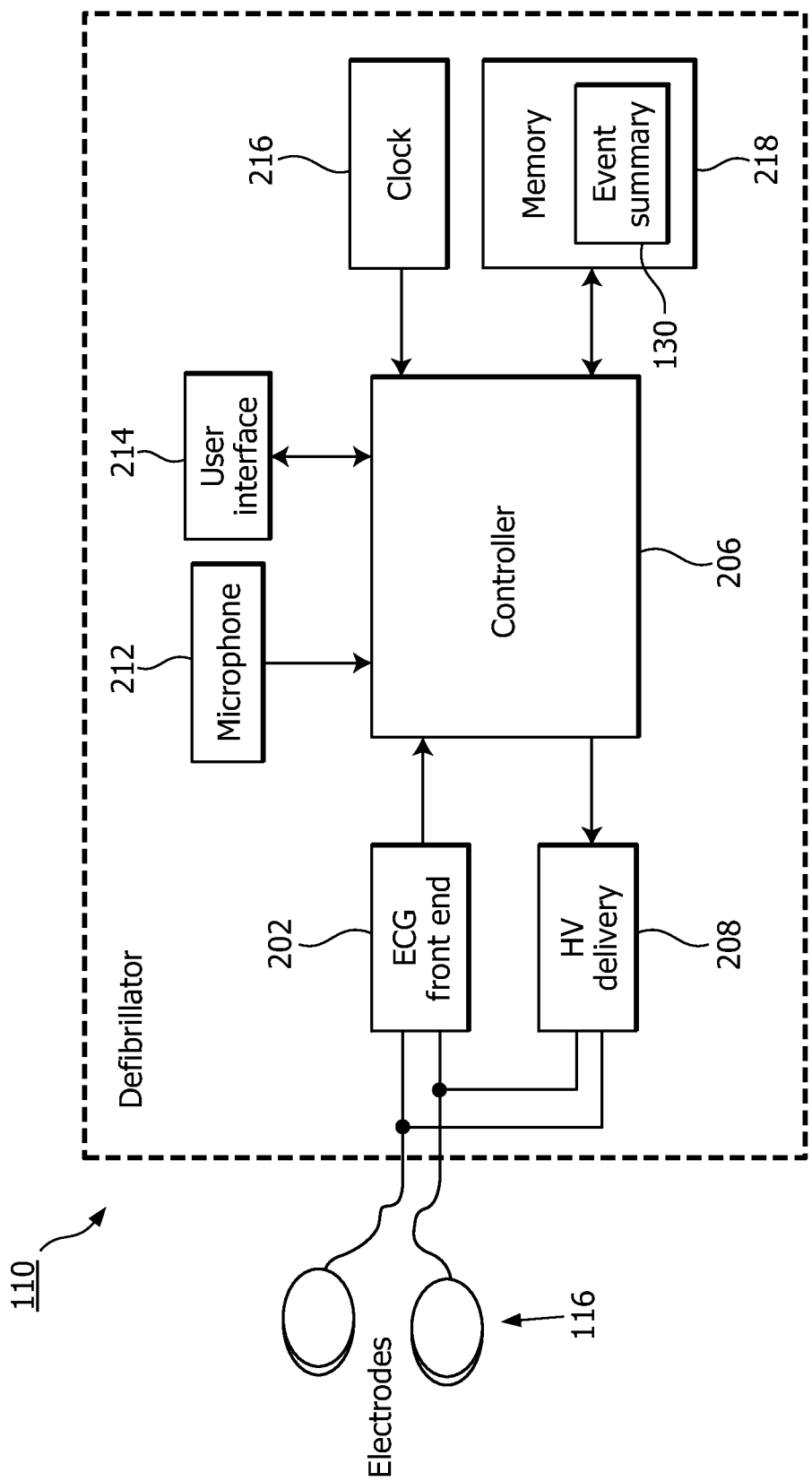
FIG. 2 is a block diagram of a defibrillator constructed in accordance with the principles of the present invention.

FIG. 2 illustrates a defibrillator 110 constructed in accordance with the principles of the present invention. For purposes of the discussion that follows, the defibrillator 110 is configured as an AED, and is designed for small physical size, light weight, and relatively simple user interface capable of being operated by personnel without high training levels or who otherwise would use the defibrillator 110 only infrequently. In contrast, a paramedic or clinical defibrillator of type generally carried by an emergency medical service (EMS) responder tends to be larger, heavier, and have a more complex user interface capable of supporting a larger number of manual monitoring and analysis functions. Although the present embodiment of the invention is described with respect to application in an AED, other embodiments include application in different types of defibrillators, for example, manual defibrillators, and paramedic or clinical defibrillators.

An ECG front end circuit 202 is connected to a pair of electrodes 116 that are connected across the chest of the patient 14. The ECG front end circuit 202 operates to amplify, buffer, filter and digitize an electrical ECG signal generated by the patient's heart to produce a stream of digitized ECG samples. The digitized ECG samples are provided to a controller 206 that performs an analysis to detect VF, shockable VT or other shockable rhythm and, in accordance with the present invention, that performs an analysis to determine a treatment regimen which is likely to be successful. If a shockable rhythm is detected in combination with determination of a treatment regimen that indicates immediate defibrillation shock, the controller 206 sends a signal to HV (high voltage) delivery circuit 208 to charge in preparation for delivering a shock and a shock button on a user interface 214 is activated to begin flashing. When the user presses the shock button on the user interface 214 a defibrillation shock is delivered from the HV delivery circuit 208 to the patient 14 through the electrodes 116.

The controller 206 is coupled to further receive input from a microphone 212 to produce a voice strip. The analog audio signal from the microphone 212 is preferably digitized to produce a stream of digitized audio samples which may be stored as part of an event summary 130 in a memory 218. The user interface 214 may consist of a display, an audio speaker, and control buttons such as an on-off button and a shock button for providing user control as well as visual and audible prompts. A clock 216 provides real-time clock data to the controller 206 for time-stamping information contained in the event summary 130. The memory 218, implemented either as on-board RAM, a removable memory card, or a combination of different memory technologies, operates to store the event summary 130 digitally as it is compiled over the treatment of the patient 14. The event summary 130 may include the streams of digitized ECG, audio samples, and other event data as previously described.

The AED of FIG. 2 has several treatment rescue protocols or treatment modes which may be selected during setup of the AED when it is initially received by the EMS service. One type of protocol is the "shock first" protocol. When the AED is set up for this protocol, the AED will, when connected to a patient and activated, immediately analyze the patient's ECG heart rhythm to make a heart rhythm classification. If the analysis determines that an arrhythmia treatable with electrical defibrillation is present, typically either ventricular fibrillation (VF) or pulseless ventricular tachycardia (VT), the rescuer is informed and enabled to deliver the shock. If it is determined that the arrhythmia is not treatable with a defibrillation shock, the AED will go into a "pause" mode during which CPR may be performed.

The second type of protocol is the "CPR first" protocol. When the AED is set up for this protocol, the AED will begin operating by instructing the rescuer to administer CPR to the patient. After CPR is administered for a prescribed period of time, the AED begins to analyze the ECG data to see if an arrhythmia treatable with electrical defibrillation is present.

In accordance with the principles of the present invention the AED 110 has a third setup, which is to initially recommend a treatment protocol, either shock first or CPR first. This is done by the AED which begins by analyzing the patient's ECG waveform, calculating and evaluating a ROSC score as described below. From the evaluation of the ROSC score a treatment protocol is recommended. The recommended protocol may be immediately carried out by the AED, or the recommendation presented to the rescuer for his or her final decision on the treatment protocol to be carried out.

Figure 3:
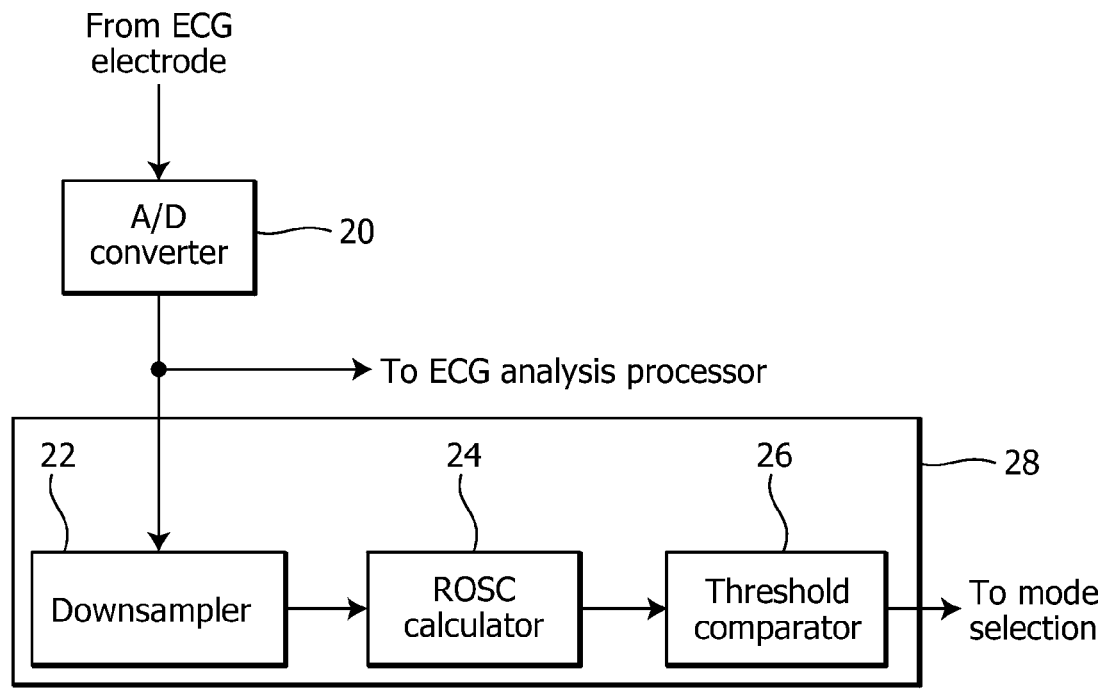
FIG. 3 is a detailed block diagram of a ROSC predictor constructed in accordance with the principles of the present invention.

FIG. 3 illustrates a portion of the ECG front end circuit 202 and controller 206 which operate in accordance with the principles of the present invention. As previously mentioned the electrodes 116 provide ECG signals from the patient which are sampled (digitized) by an A/D converter 20. The digitized ECG signals are coupled to the ECG analysis processor circuit in the controller which analyzes the ECG waveform to determine whether application of a shock is advised. The ECG samples are also coupled to a treatment decision processor 28 comprised of an optional downsampler 22, a ROSC calculator 24 and a threshold comparator 26. Optional downsampler 22 subsamples the stream of ECG samples to a lower data rate. For instance, a data stream of 200 samples/sec may be downsampled to 100 samples/sec. The ECG data samples are coupled to a ROSC calculator 24 which determines a ROSC score from the ECG data. The ROSC score is compared against a threshold by threshold comparator 26 to determine a mode of treatment which is most likely to lead to a successful resuscitation. This mode determination is coupled to the mode selection portion of the controller, which either selects the desired mode automatically or presents the mode as a recommendation to the rescuer who may then either decide to follow the recommended mode or an alternate treatment regimen. Although the treatment decision processor 28 is shown as a separate element from the controller 206, it is understood that the treatment decision processor 28 and the ECG analysis processor circuit may be part of control or 206.

The ROSC calculator 24 may be operated in several ways. For one example, the ROSC score is calculated as the mean magnitude of the bandwidth limited first derivative (or first difference, which is a discrete-time analog) of the ECG over a period of a few seconds. Since the bandwidth limited first derivative may already be calculated for arrhythmia detection by the controller 206, the additional computation may involve only the additional calculation of an average absolute value. This process can be implemented as a real-time measure by means of a moving average requiring only one addition and one subtraction per sample. For instance, the difference of successive samples may be taken for a stream of samples received over a period of 4.5 seconds at a 100 sample/sec rate. The signs of the differences are discarded to produce absolute values, which are summed over the 4.5 second period. This produces a ROSC score value which is equivalent to a frequency-weighted average amplitude of the ECG waveform. The score may be scaled or further processed in accordance with the architecture and demands of the instant system.

Since the spectrum of the first derivative is proportional to frequency, the ROSC score is largely unaffected by CPR artifact, most of which will be very low frequency. Thus, a ROSC score calculated in this way is capable of providing meaningful information about the vitality of the patient's heart during CPR.

Another alternative way to calculate a mean value is to square the differences of the consecutive samples, then sum the products and take the square root of the sum. This produces an RMS (root mean square) form of ROSC score.

As an alternative to the mean value computation, another approach is to use the median magnitude of the first derivative. This approach is more computationally intensive, but can advantageously be more robust to noise. Care must be taken to avoid de-emphasizing the signal that gives the measure its discriminating power. In another embodiment, a trimmed mean or min-max calculation can offer a favorable compromise. By eliminating the largest outliers, greater immunity to impulse artifacts (e.g. physical disturbances of the electrode pads) can be provided. By eliminating the largest outliers, the occasional high amplitude artifact which would occur relatively infrequently can be eliminated without significantly reducing the discriminating power associated with the data of cardiac origin.

An AED has been constructed to operate in accordance with the present invention. The inventors have discovered that the implemented ROSC score processor identifies ECG rhythms which result in ROSC following immediate defibrillation with high sensitivity, e.g., around 90%, and specificity greater than 60%. Sensitivity (Sn) is the percentage of patients that would achieve ROSC in response to an immediate defibrillation shock, that are correctly identified by the ROSC score. Specificity is the percentage of patients that would not achieve ROSC in response to an immediate defibrillation shock, that are correctly identified by the ROSC score. Sensitivity and specificity with respect to ROSC may be traded off in approximately equal proportion.

Figure 4:
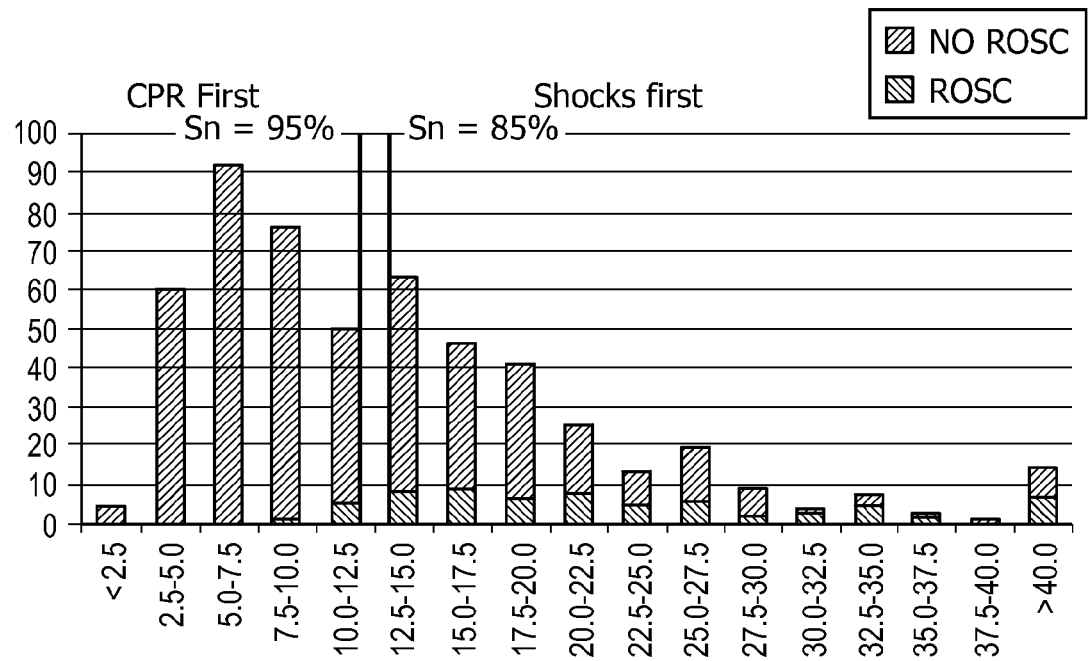
FIG. 4 is a graph of patient data illustrating the determination of a threshold which can be used in the ROSC predictor of FIG. 3.

An implementation whereby alternative setup sensitivities were made available to the user is shown by the graph of FIG. 4. A database was assembled of the results of patients treated with defibrillation, some of whom achieved ROSC in response to an initial defibrillation shock and some of whom did not. The patients were treated after varying cardiac arrest durations. The ROSC score calculated by the implemented system was in the range of 2.5 to 40.0 units, where each unit corresponds to 0.25 mV/sec. The more lightly shaded portions of the bars in the graph indicate patients in the database who exhibited ROSC after delivery of a shock. The more darkly shaded portions of the bars indicate patients who did not exhibit ROSC after treatment. The graph shows the results of ROSC scoring by the system, which exhibited a 95% sensitivity to ROSC following an initial shock for patients with ROSC score greater than 3.0 mV/sec (i.e. 12.0 units), and a sensitivity of 85% for patients with ROSC score greater than 3.6 mV/sec (i.e. 14.4 units). Below a ROSC score of about 2.5 mV/sec (i.e. 10 units), 100% of the patient population failed to achieve ROSC as the result of a first shock and may have benefited from a CPR first regimen of treatment. In the implemented system two thresholds of different sensitivities were used, one of 95% sensitivity and the other of 85% sensitivity. The user is thus able to select a desired sensitivity during setup of the AED and can favor greater use of shock first with selection of the higher sensitivity (95%) or greater use of CPR first with a lower sensitivity (85%).

The implemented system has also been found to identify a good outcome population for patients treated with a shocks-first protocol, experiencing neurologically intact survival of 53%, (95% CI [40%, 67%]). The implemented system also identified a poor outcome group that achieved neurologically intact survival of only 4%, (95% CI [0.1%, 20%]) and who might therefore benefit from CPR-first resuscitation.

Figure 5:
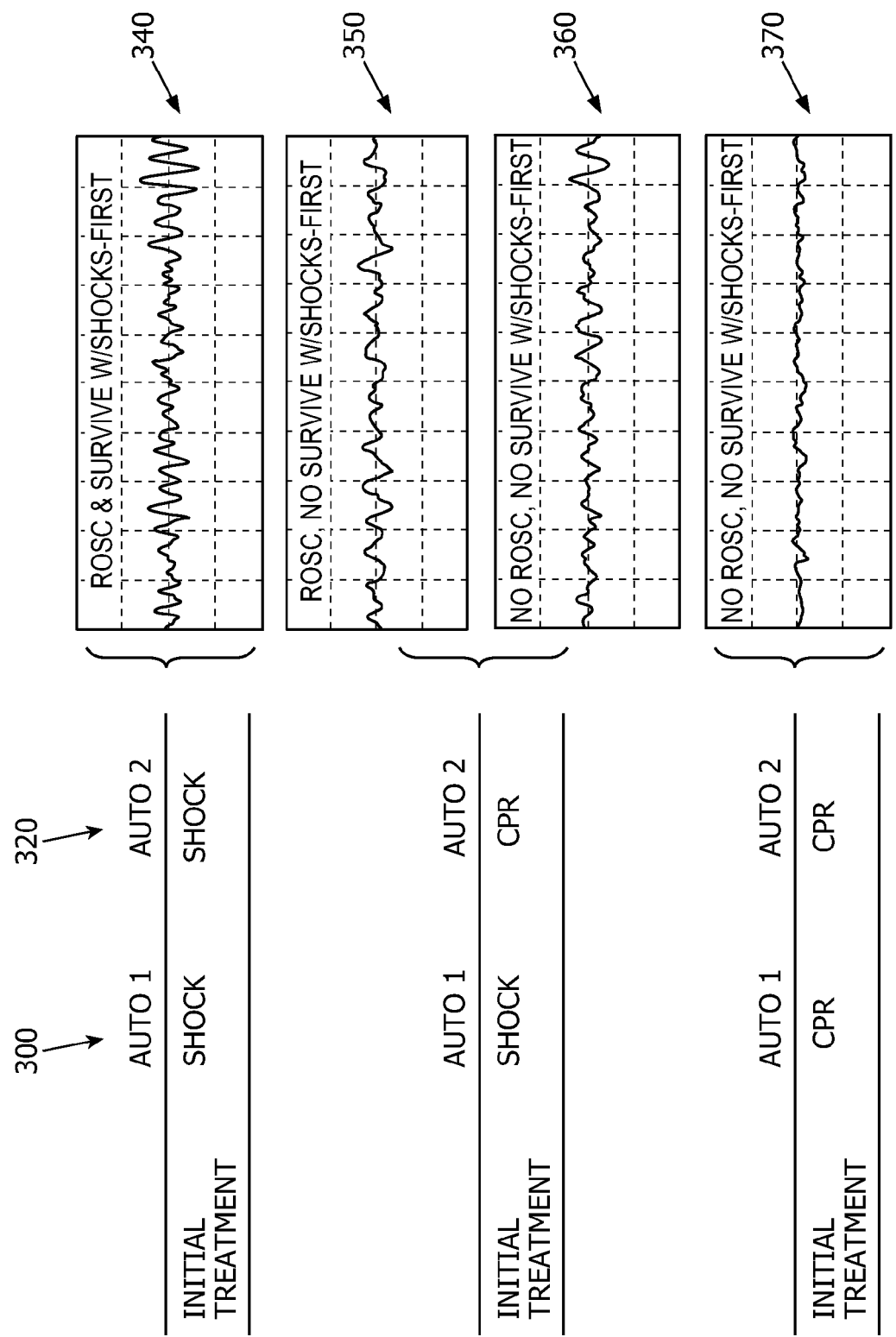
FIG. 5 illustrates the results obtained by the constructed system for four ECG waveforms with different sensitivity settings.

FIG. 5 illustrates the results obtained by the constructed system for four ECG waveforms with different sensitivity settings. In the Auto 1 (higher) sensitivity setting 300, a shock-first is advised in response to the first three ECG waveforms 340, 350, 360 and CPR-first is advised for the fourth 370. In the Auto 2 (lower) sensitivity setting 320 a shock-first is advised for the first ECG waveform 340 and CPR-first is advised for the other three ECG waveforms 350, 360, 370.

An alternative embodiment to the invention uses an AED shock advisory algorithm designed for high specificity, and an index of ECG rate of change (called vRhythm, as described in U.S. patent application Ser. No. 11/917,272) that is indicative of the likelihood of ROSC after a defibrillation shock. In artifact free ECG, at first presentation of a patient in VF, these two algorithms are used to advise either an immediate shock or an initial interval of CPR. In this case if the AED shock advisory algorithm indicates a shockable rhythm, the vRhythm score is compared to a threshold value—if it is greater than or equal to the threshold, a shock is advised, and if less than the threshold CPR is advised. A database of resuscitations has shown that for initial shockable rhythms with vRhythm below a threshold of 14.5 units, patients are very unlikely to survive if shocked immediately, and therefore may benefit from an initial period of CPR.

As the resuscitation progresses, after a defibrillation shock has been delivered, present protocols recommend a continuous interval of uninterrupted CPR (typically 2 minutes). It is common however for a patient to re-fibrillate during the CPR interval. The presence of a vigorous VF waveform in the ECG may indicate a high likelihood of ROSC if a shock were to be given immediately, whereas for the same patient, continued CPR may result in a decrease in the likelihood of ROSC. Because the fraction of patients who may benefit from an immediate shock is much less that those that would benefit from continuous CPR, pausing CPR to accurately assess the patient rhythm would interrupt CPR and possibly decrease the survival of many more patients than it would help.

This embodiment applies an AED shock advisory algorithm and the vRhythm score during CPR corrupted ECG after an initial or subsequent shock, in order to evaluate the likelihood of a vigorous shockable rhythm without ceasing CPR. If there is a high likelihood of a shockable rhythm as indicated by a high vRhythm score, CPR would be stopped, and a shock delivered after a confirming analysis in artifact free ECG. Future algorithm enhancements that identify very high likelihood of a shockable rhythm during CPR may allow shock delivery without an intervening confirmatory analysis. This embodiment would therefore allow delivering an immediate shock to patients whose survival may be improved by an immediate shock, without compromising resuscitation of other patients who may benefit more by continuing CPR.

Figure 6:
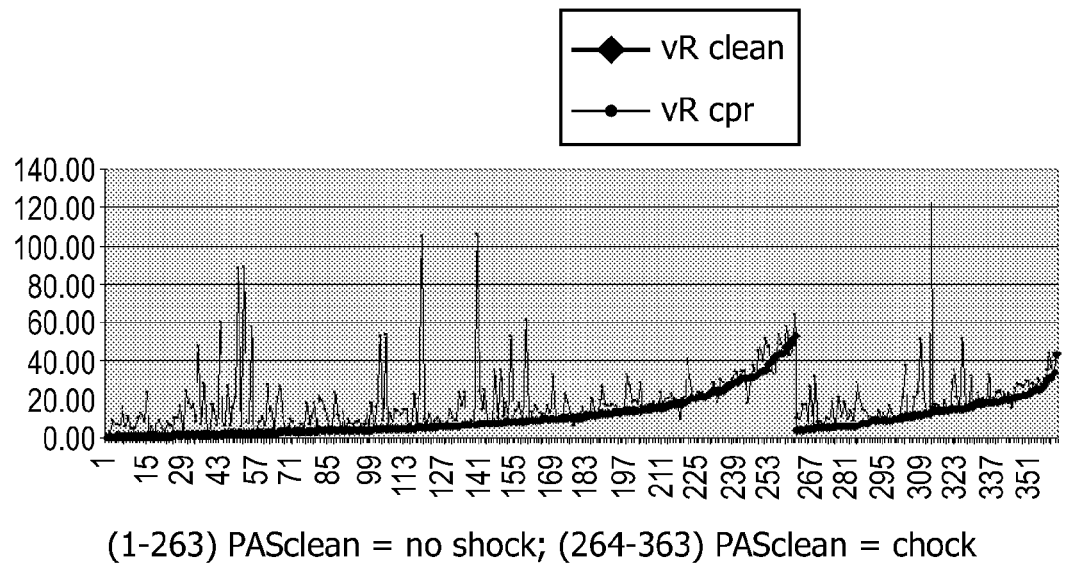
FIG. 6 illustrates the vRhythm score during clean data (vRclean) and during CPR corrupted data (vRcpr).

Turning now to FIG. 6, an implementation of the present invention has been evaluated using the Philips Patient Analysis System (PAS) shock advisory algorithm, in conjunction with the Philips vRhythm score. Improvements in performance of the reported embodiment may be gained through simple modification of each of these algorithms within the scope of this description. To evaluate performance, an ECG database, adapted from the "Sister's" database compiled by Laerdal Medical, Wappinger Falls, N.Y., includes ECG data from resuscitations with a wide variety of rhythms representative of those expected in practice. The database contains 20-second ECG strips, the first 10 seconds recorded during CPR, followed by 10 seconds after CPR cessation. Measurements and results from the algorithms for these two data segments will be referred to in this description by subscripts 'cpr' and 'clean'.

The PAS results and vRhythm score were used on data from the clean ECG segment to establish a 'truth annotation' for each case in the database. In conformance with the previous Philips vRhythm invention, cases for which the PAS result indicated 'shock advised' and for which the vRhythm score was greater than or equal to 14.5 were annotated as 'true' for high likelihood of benefit from ceasing CPR for delivery of a defibrillation shock (referred to hereafter as 'True Stop CPR'). Because the CPR and clean data segments are continuous in time, this truth annotation determined in the clean data is assumed to also be true for the CPR corrupted data (i.e. the underlying rhythm is assumed not to change during the 20 second recording). Hence this database allows us to evaluate performance in the CPR corrupted data and compare it to the 'truth' determined from the clean ECG data.

FIG. 6 shows the vRhythm score during clean data (vRclean) and during CPR corrupted data (vRcpr) for all 363 cases in the database. The cases have been sorted for increasing vRclean and PAS decision in the clean data segment (PASclean). For cases 1-263 PASclean was no shock, and for cases 264-363 PASclean was shock (100 cases). Cases 324-363 (40 cases) met the criteria for 'True Stop CPR', i.e. rhythms for which the patient would be judged likely to benefit from an immediate shock instead of continued CPR. The remaining cases (1-323) are 'False Stop CPR', or also referred to as 'True Continue CPR'.

FIG. 6 also shows vRcpr in direct comparison with the vRclean value. The figure shows that CPR artifact biases the vRhythm score toward larger values. To accommodate this bias, for vRhythm evaluated during CPR, this implementation raises the threshold for indicating an immediate shock to greater than or equal to 19 (instead of the 14.5 threshold for clean data). Also note that there are several extreme values of vRcpr uncharacteristic of values for vRclean. Hence this implementation includes a vRcpr threshold of 50, above which CPR will not be interrupted.

Figure 7:
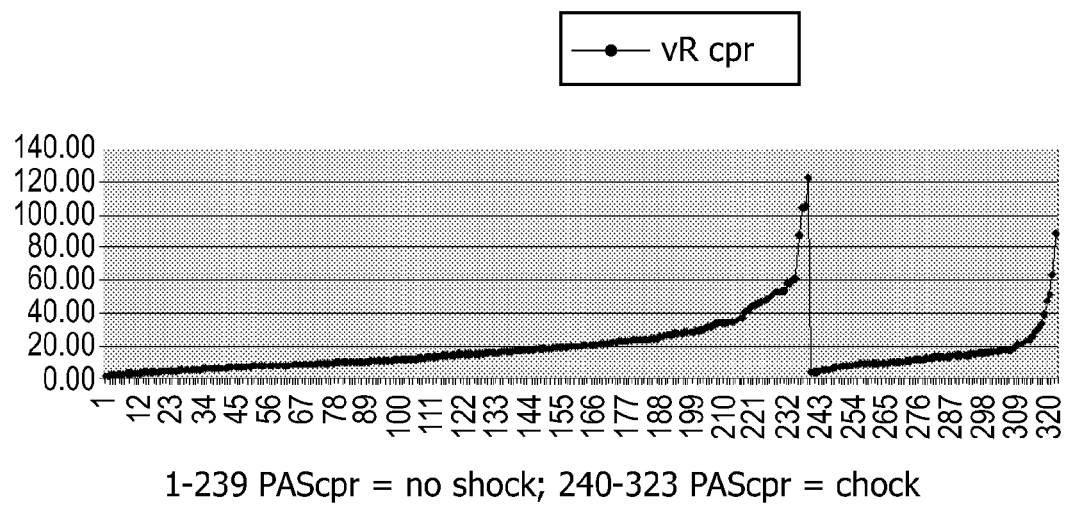
FIG. 7 shows vRhythm during CPR (vRcpr) for the 'True Continue CPR' cases from FIG. 6.

Turning now to FIG. 7, shown is vRhythm during CPR (vRcpr) for the 'True Continue CPR' cases from FIG. 6. In FIG. 7 the data is sorted by vRcpr and by PAS decision for the CPR corrupted data segment (PAScpr). This data allows determining false positive and true negative Stop CPR performance. There are 11 false positive cases (310-320) for which (PAScpr=shock) and (19<vRcpr<=50). There are 312 true negative cases: (1-309) and (321-323).

Figure 8:
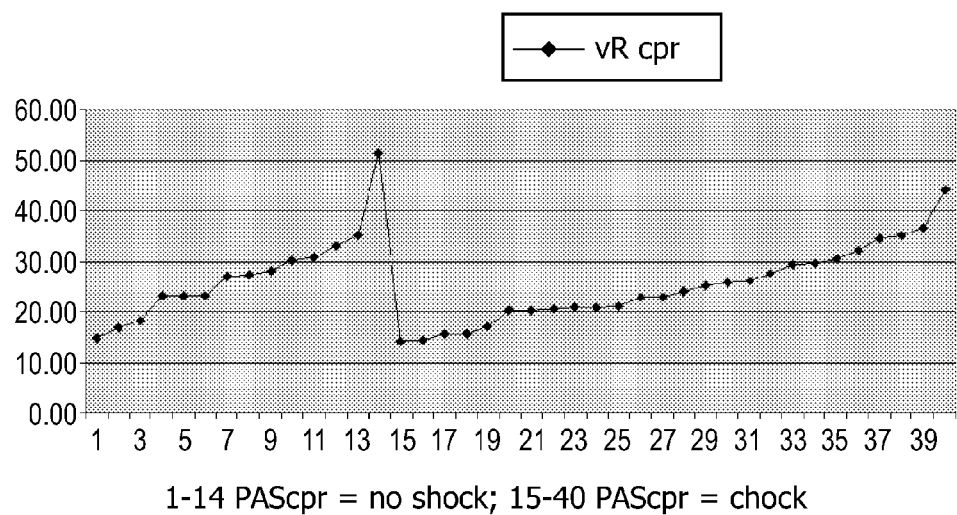
FIG. 8 shows vRcpr for the 'True Stop CPR' cases from FIG. 6.

FIG. 8 shows vRcpr for the 'True Stop CPR' cases from FIG. 6. In FIG. 8 the data is sorted by vRcpr and by PAS decision for the CPR corrupted data segment. This data allows determining true positive and false negative Stop CPR performance. There are 19 false negative cases: cases 1-14 because PAScpr=no shock and cases 15-19 because vRcpr <19. There are 21 true positive Stop CPR cases (20-40).

Combined, the performance data from FIGS. 7 and 8 can be used to calculate the sensitivity, specificity, and positive predictivity of the criteria that, during CPR, predict the cases from this database for which interrupting CPR to deliver a rescue defibrillation shock would be potentially beneficial. The data indicate the following: sensitivity=53%; specificity=97%; positive predictivity=66%.

For CPR periods of the prior art defibrillators, CPR must be either continuous for all patients, or interrupted for all patients to assess the need to deliver of a defibrillation shock. For continuous CPR, 323 cases from this dataset would receive the most likely optimal therapy (89%), and 40 cases that may benefit from an early shock would receive suboptimal therapy (11%). Interrupting all rescues for assessing the need to deliver a shock would result in suboptimal therapy for 323 cases (89%), and more optimal therapy for 40 cases (11%). In accordance with the present invention, however, CPR would be interrupted for 32 cases (21 true positive and 11 false positive, 9%); and CPR would be continuous for 331 cases (19 false negative and 312 true negative). Therapy would be optimal in 333 cases (21 true positive and 312 true negative, 92%), and suboptimal in only 30 cases (11 false positive and 19 false negative, 8%). Thus, the overall performance of the inventive vRhythm algorithm that determines a ROSC score during CPR results in better performance than the prior art CPR protocols. For the purposes of clarity, the term "ROSC score" is used hereafter to refer to the vRhythm score determined by the vRhythm algorithm as described above.

It is well known to those skilled in the art that adjustments to the algorithm criteria will alter these performance statistics. It is also well known that the performance criteria depend on the relative incidence of rhythms in the database on which they are calculated. This database appears representative of many emergency response systems throughout the world for which survival from cardiac arrest is very low, hence the low incidence of cases for which stopping CPR might be beneficial. For other systems with shorter response times, and hence higher survival rates, the incidence of cases for which stopping CPR might be beneficial will be higher, and the benefit of the algorithm will be correspondingly greater.

In an alternative embodiment of the invention, for example, the algorithm could be adjusted to calculate scores only during detected short breaks in the CPR compressions, i.e. when low artifact noise levels occur. The detection could be obtained through secondary indicators of motion, such as a chest-applied accelerometer, common mode current, transthoracic impedance changes, or via ECG signal analysis. Enough data may be accumulated during a sufficient number of these short breaks to indicate a likelihood that refibrillation has occurred during CPR. If so indicated, the AED could direct a pause for further analysis. If a false negative has improperly caused the AED to foreshorten CPR, then the analysis may be additionally adjusted, filtered, or shut off entirely for subsequent CPR periods.

This embodiment of the invention evaluated one set of criteria. Other embodiments may alter these criteria, or modify the two algorithms to which the criteria are combined. For example, the shock advisory algorithm may be adjusted to produce fewer false negative cases by altering criteria within it, and the vRhythm calculation may also be modified (e.g. modified bandwidth) to further suppress the effects of CPR artifact on the ROSC score. Previous ROSC scores, including the presenting ROSC score, may also be used as input to a decision on whether to interrupt CPR for a defibrillation shock. Furthermore, this embodiment of the invention has used only ECG data in its estimation of the need to deliver a defibrillation shock. Other signals, gathered simultaneously with the ECG (e.g. patient small-signal impedance, common mode current, and chest wall acceleration during CPR) may allow further optimization of an embodiment of the invention.

Figure 9:
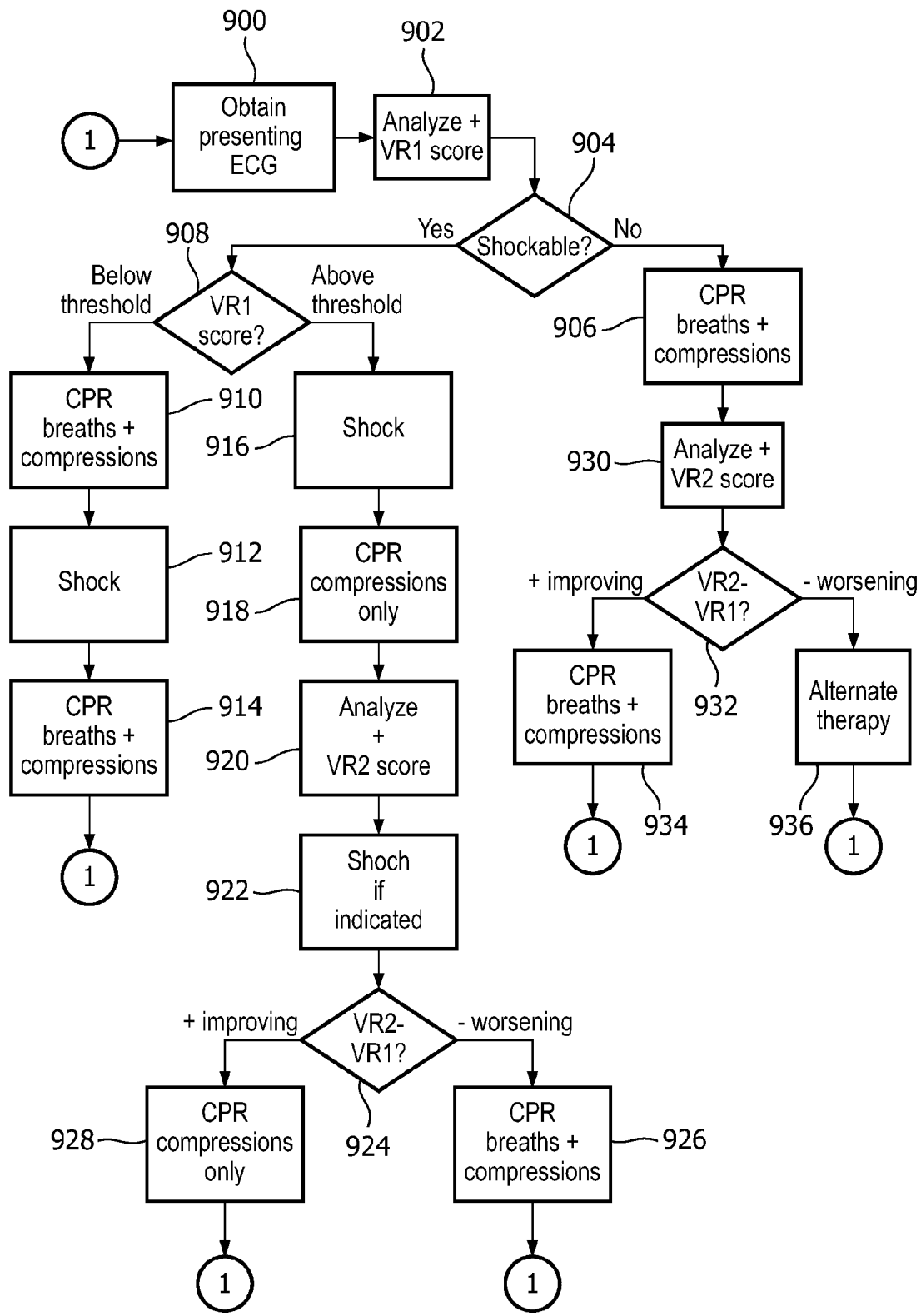
FIG. 9 shows a procedural flow diagram of decisions for CPR and defibrillation during a cardiac rescue, using the trends in vRhythm score and the shock determination algorithm.

Turning now to FIG. 9, a flow chart showing automatic decision-making criteria in an AED is shown. Organizations continue to emphasize simpler CPR in an effort to increase survival and encourage bystanders to act. f hands-only CPR is a better alternative (for the particular rhythm) then that would help simplify CPR. If breaths are not necessary, it will minimize interruptions for giving breaths and promote survival. The rescue protocol described in the flow chart takes into account these principles to offer simpler and more effective CPR when possible.

In FIG. 9, once the electrodes are attached to the cardiac arrest patient, the AED obtains an ECG at step 900. At step 902, the AED employs its analysis algorithm to determine whether the ECG is shockable or not and employs its vRhythm algorithm, as described previously, to calculate a ROSC score VR1. If the rhythm is non-shockable, step 904, the AED enters a first CPR mode of operation, defined as CPR with rescue breaths and compressions at step 906. If the ECG is shockable, then the ROSC score VR1 is compared to a threshold score at step 908. If the ROSC score VR1 is low, then the AED enters a shock-first protocol, and immediately directs the first CPR mode of operation at step 910 followed by a defibrillating shock at step 912 and another period of first CPR mode of operation at step 914.

If the ECG is shockable with a ROSC score above threshold at step 908, then the AED immediately directs a shock at step 916 followed by a second CPR mode of operation at step 918. Here, the second CPR mode of operation is defined as CPR with compressions only. The reason for this decision is that a patient having a high ROSC score VR2 may benefit more from compressions-only CPR.

FIG. 9 also shows that following the first shock/CPR interval, the ECG is again analyzed at step 920. The AED calculates a second ROSC score VR2, and compares VR2 with the first ROSC score VR1 at decision step 924. An increase in ROSC score indicates "good" CPR and/or improving chance of survival. Thus, after a shock, if the ROSC score increases, then the AED continues the second CPR mode of operation at step 928. A decreasing ROSC score, however, indicates a worsening chance of survival, perhaps exacerbated by "poor" CPR. If the ROSC score falls, then, the AED directs a change to the first CPR mode of operation at step 926.

For a non-shockable presenting ECG, the AED applies at step 906 the first CPR mode of operation without a defibrillating shock. After the CPR period, the AED repeats the ECG analysis and calculates a subsequent ROSC score VR2 at Step 930. The AED then compares VR2 with the first ROSC score VR1 at decision step 932. An increase in ROSC score indicates "good" CPR and/or improving chance of survival. Thus, if the ROSC score increases, then the AED continues the second CPR mode of operation at step 934. A decreasing ROSC score, however, indicates a worsening chance of survival, perhaps indicating that CPR is ineffective. Thus a falling ROSC score in this arm causes the AED to change from a first CPR mode of operation to an alternate therapy at step 936. The alternate therapy could be the second CPR mode of operation, or directing the use of pharmaceutical therapy such as epinephrine, hypothermia therapy or other known cardiac rescue techniques.

At the end of any of the protocol branches indicated by the circled "1" in FIG. 9, the cardiac rescue may progress in accordance with prior art protocols. More preferably, the inventive method may be continued by returning to step 900 for further subsequent analysis. Repetition of the method throughout the rescue enables the continued adjustment of the rescue protocol as warranted by a change in the patient's ECG. Further adjustment of the ROCS score thresholds or decision criteria could occur, for example, when step 900 is re-entered following a confirmed application of the alternate therapy at step 936.

Figure 10:
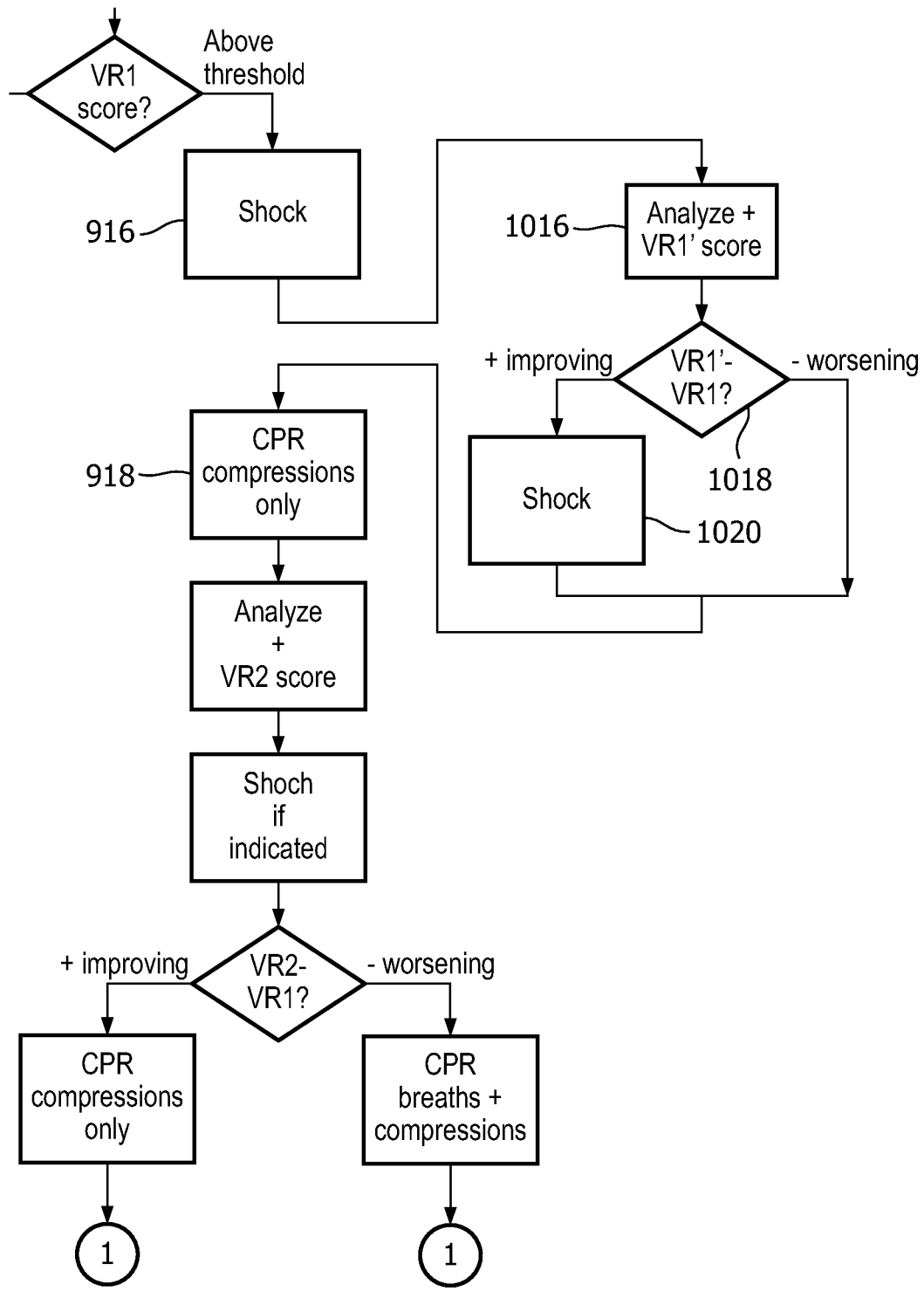
FIG. 10 shows a procedural flow diagram of decisions for whether to issue a supplemental defibrillating shock based on the trend of the vRhythm score from just before to just after a first shock.

Another embodiment of the invention is shown in the flow chart of FIG. 10. FIG. 9 illustrates a conventional shock delivery protocol having a pre-set number of shocks to be delivered prior to the next CPR period; in this instance a single-shock protocol. The inventors have discovered that a ROSC score which is calculated immediately following the shock can indicate whether or not a supplemental shock would benefit the patient prior to entering the CPR period. In effect, this embodiment uses the ROSC score to adjust the number of shocks to be delivered in a series prior to continuing the rescue.

FIG. 10 shows a modified decision process which is inserted between the FIG. 9 step 916 and step 918 Immediately following the shock at step 916, the AED obtains ECG data and calculates a subsequent ROSC score VR1' at step 1016. The AED then compares VR1' with the first ROSC score VR1 at decision step 1018. An increase in ROSC score indicates an improving chance of survival even if the ECG rhythm has not been converted by the shock, so a supplemental shock may be warranted. The AED thus arms and directs a supplemental shock to be delivered prior to initiating the CPR period of step 918. A worsening ROSC score detected at step 1018, however, may indicate that immediate CPR is better for the patient. In this case, the AED initiates CPR step 918 without further delay.

Yet another embodiment of the invention is shown in the flow chart of FIG. 11. FIG. 11 illustrates the use during a CPR period of a ROSC score VR3 to optimize therapy in accordance with the discoveries of FIGS. 7 and 8. Here shown is the CPR period of FIG. 9 step 910 although it is understood that the inventive method may be incorporated into any or all of the CPR periods herein described.

The embodiment of FIG. 11 illustrates an AED treatment decision processor which captures ECG data during the CPR period 910. The AED calculates a ROSC score VR3 at step 1110 and compares VR3 to a threshold at step 1112. A ROSC score VR3 below the threshold indicates a low probability of a shockable rhythm. The AED in this case thus directs the continued application of CPR at step 1114.

A ROSC score VR3 above the threshold, however, indicates a high likelihood of a shockable rhythm, i.e. sufficiently vigorous to be converted by immediate shock. The AED in this event directs the interruption of CPR at step 1116 by means of the aural and/or visual outputs of user interface 214. The AED subsequently detects the cessation of CPR in step 1118, by any of the previously described methods including common mode current, patient impedance or secondary chest wall compressions sensors. Then the AED analyzes the ECG data to confirm the presence of a shockable rhythm at step 1120.

If a shockable rhythm is confirmed in step 1122 of FIG. 11, the AED arms and directs the application of a defibrillating shock in step 1124. After the shock is delivered, CPR is resumed at step 1126 until the end of the CPR period.

The analysis step 1120 may instead indicate that ROSC score VR3 is a false positive caused by CPR artifact. In this case, it is important that the false positive does not recur in subsequent CPR periods in order to ensure uninterrupted compressions. So the AED responds to a false positive ROSC score VR3 by directing the immediate resumption of CPR in step 1128. In addition, the AED preferably reduces the sensitivity of the ROSC scoring threshold used in step 1112 at step 1130.

Alternatives to the aforedescribed procedure are envisioned by this invention. For example, the CPR mode of operation directed by the AED in the presence of a shockable, low initial ROSC score might be the first CPR mode of operation instead of the second CPR mode of operation. The CPR mode of operation directed by the AED, after the shock and in the presence of a degrading (i.e. falling) vRhythm score might be the second CPR mode of operation instead of the first CPR mode of operation. These alternatives would be employed based upon an assessed quality of CPR.

Another alternative is to employ a threshold score as the decision criteria for changing the first CPR mode of operation to the second CPR mode of operation, instead of using a mere increasing or decreasing score criteria. This technique would likely result in fewer adjustments in CPR mode of operation, which could reduce confusion during the rescue somewhat. In addition, using a threshold comports somewhat more closely with the analytical basis of the invention.

What is claimed is:

1. A defibrillator comprising:
   an ECG front end circuit coupled to a source of ECG signals; and
   a controller communicatively coupled to the ECG front end circuit, comprising
   an ECG data analysis circuit responsive to the ECG signals which analyzes ECG data to determine whether a shock is recommended or a shock is not recommended; and
   a treatment decision processor responsive to the ECG signals which acts to estimate a first probability of resuscitation from a shock and a subsequent probability of resuscitation from a shock; and
   a defibrillator mode circuit responsive to the ECG data analysis circuit and the treatment decision processor which is operable to set the defibrillator to a shock mode or a CPR mode of operation and which is further operable to change a CPR mode of operation from one of a plurality of CPR modes of operation to another one of a plurality of CPR modes of operation based on a change from the first probability to the subsequent probability,
   wherein the plurality of CPR modes of operation comprises a compressions-only mode and a compressions-plus-breaths mode of operation, and further wherein the defibrillator mode circuit changes the CPR mode of operation from a compressions-only mode to a compressions-plus-breaths mode of operation if the subsequent probability is lower than the first probability.

2. The defibrillator of claim 1, wherein the treatment decision processor comprises a ROSC calculator which estimates the first and subsequent probabilities of resuscitation as a first ROSC score and a subsequent ROSC score.

3. The defibrillator of claim 1, wherein the defibrillator mode circuit alternates the shock mode of operation with the CPR mode of operation regardless of which of the plurality of CPR modes of operation is selected.

4. The defibrillator of claim 1, further comprising
   a user interface, responsive to the controller, which outputs user information relating to the change from the first probability to the subsequent probability.

5. A defibrillator comprising:
   an ECG front end circuit coupled to a source of ECG signals; and
   a controller communicatively coupled to the ECG front end circuit, comprising
   an ECG data analysis circuit responsive to the ECG signals which analyzes ECG data to determine whether a shock is recommended or a shock is not recommended; and
   a treatment decision processor responsive to the ECG signals which acts to estimate a first probability of resuscitation from a shock and a subsequent probability of resuscitation from a shock; and
   a defibrillator mode circuit responsive to the ECG data analysis circuit and the treatment decision processor which is operable to set the defibrillator to a single-shock mode or a CPR mode of operation and which is further operable to supplement the single-shock mode of operation with one additional shock to be delivered prior to a subsequent CPR period based on a change from the first probability to the subsequent probability.

6. The defibrillator of claim 5, wherein the defibrillator mode circuit supplements the shock mode of operation if the subsequent probability is higher than the first probability.

7. The defibrillator of claim 4, wherein the user interface outputs aural information.

8. The defibrillator of claim 4, wherein the user interface outputs visual information.

9. A method for delivering electrotherapy from a defibrillator comprising the steps of: receiving patient ECG signals;
   determining from the ECG signals the presence of an arrhythmia treatable by the defibrillator;
   estimating from the ECG signals a first probability of resuscitation shock success;
   selecting a treatment protocol based upon both of the determined treatable arrhythmia and the estimated first probability of resuscitation;
   estimating from subsequent ECG signals a subsequent probability of resuscitation shock success;
   comparing the first and subsequent probabilities of resuscitation shock success; and
   selecting a second treatment protocol if the subsequent probability is lower than the first probability from the comparing step,
   wherein the treatment protocol is a compressions-only mode of CPR operation and the second treatment protocol is a compressions-plus-breaths mode of CPR operation.

10. The method of claim 9, further comprising;
    delivering a supplementary electrotherapeutic shock based upon the comparing step.

11. The method of claim 10, further comprising the step of wherein estimating further comprises computing a ROSC score.

12. The method of claim 10, wherein estimating further comprises comparing the ROSC score to a threshold.

* * * * *